(12) United States Patent
Smith (10) Patent No.: US 9,468,449 B2
(45) Date of Patent: Oct. 18, 2016

(54) RECONSTRUCTIVE JOINT TUNNEL DRILLING LOCATOR

(75) Inventor: Graham Smith, Newburyport, MA (US)

(73) Assignee: Smith & Nephew, Inc., Memphis, TN (US)

( * ) Notice: Subject to any disclaimer, the term of this patent is extended or adjusted under 35 U.S.C. 154(b) by 872 days.

(21) Appl. No.: 13/076,766

(22) Filed: Mar. 31, 2011

(65) Prior Publication Data

US 2012/0253352 A1    Oct. 4, 2012

Related U.S. Application Data (60) Provisional application No. 61/419,054, filed on Dec. 2, 2010.

(51) Int. Cl.
| | | |
|---|---|---|
| A61B 17/58 | (2006.01) | |
| A61B 17/17 | (2006.01) | |
| A61B 17/00 | (2006.01) | |

(52) U.S. Cl.
CPC .. *A61B 17/1714* (2013.01); *A61B 2017/00407* (2013.01); *A61B 2017/1778* (2013.01)

(58) Field of Classification Search
CPC .......... A61B 17/1714; A61B 17/1728; A61B 17/1757; A61B 2017/00407; A61B 2017/1778
USPC .......... 606/86 R, 87, 96–98; 623/13.11–13.2
See application file for complete search history.

(56) References Cited

U.S. PATENT DOCUMENTS

| | | |
|---|---|---|
| 5,573,538 A | 11/1996 | Laboureau |
| 5,891,150 A | 4/1999 | Chan |
| 5,968,050 A | 10/1999 | Torrie |
| 2002/0133165 A1 | 9/2002 | Whittaker et al. |
| 2002/0173849 A1* | 11/2002 | McKernan et al. ....... 623/13.14 |
| 2003/0216742 A1 | 11/2003 | Wetzler et al. |
| 2006/0271059 A1* | 11/2006 | Reay-Young et al. .......... 606/96 |
| 2007/0270804 A1 | 11/2007 | Chudik |

(Continued)

FOREIGN PATENT DOCUMENTS

| | | |
|---|---|---|
| EP | 1917921 | 5/2008 |
| FR | 2911264 | 7/2008 |
| WO | 0140748 | 6/2001 |

OTHER PUBLICATIONS

International Search Report and Written Opinion mailed Jun. 1, 2012 in corresponding Int'l. Application No. PCT/US2012/031482.

*Primary Examiner* — Anu Ramana
*Assistant Examiner* — Jessica Weiss
(74) *Attorney, Agent, or Firm* — Burns & Levinson LLP; Joseph M. Maraia (57) ABSTRACT

An acromioclavicular joint guide for forming multiple drill tunnels spaced apart by a predetermined distance employs two drill guides in a pivoting arrangement allowing one drill guide to pivot around the axis of the other. The drill guides are each disposed in a respective sleeve of a pivot block for insertion toward the surgical member along nonintersecting axes defined by the sleeve. An elongated arm attaches to the pivot block at a proximate end and has a aimer point at a distal end, in which the arm may extend around the surgical member via an inverted portion or bend such that the aimer point is on the insertion axis of the primary drill guide. In this manner the aimer point locates an exit of the hole from the insertion point defined by the primary drill guide, and the pivotal drill guide defines a second tunnel at the predetermined distance.

12 Claims, 6 Drawing Sheets

(56) References Cited

U.S. PATENT DOCUMENTS

2008/0103506 A1* 5/2008 Volpi et al. .................. 606/96
2008/0140748 A1  6/2008 Lada
2009/0076512 A1* 3/2009 Ammann et al. ............. 606/87
2010/0121337 A1  5/2010 Pandya

* cited by examiner

RECONSTRUCTIVE JOINT TUNNEL DRILLING LOCATOR

RELATED APPLICATIONS

This application is related to and claims the benefit of earlier filed U.S Provisional Patent Application Ser. No. 61/419,054 entitled "GUIDE FOR REPAIRING THE ACROMIOCLAVICULAR JOINT," filed on Dec. 2, 2010, the entire teachings, disclosures and contents of which are incorporated herein by reference in their entireties.

BACKGROUND

Reconstructive bone and ligament surgery often involves drilling bone tunnels into skeletal members to attach connective elements such as ligament and tendon grafts, as well as various artificial replacements and/or attachments for articulated joints. In particular, reconstructive surgery of the shoulder joint often involves reduction and drilling of the Acromioclavicular/Coracoclavicular (AC/CC) joint. Such drilling is typically facilitated by a guide for disposing an insertion wire or drilling member to an insertion location on a surgical member. Careful placement and subsequent drilling ensures maximum joint mobility from the resulting reconstruction.

SUMMARY

Reconstructive surgery for flexible joints such as arm and leg joints often involves surgical attachments that are subject to substantial force due to the pivotal movement these joints provide. Connective tissue or a suitable replacement attaches to a surgical member such as an arm or leg bone. Reconstructive surgery involving functional, structural fixation to bone members often involves drilling into a structurally sound area of the corresponding bone. Typically this involves drilling tunnels into the bone for providing a passage or attachment of a ligament. In the case of an acromioclavicular (shoulder) joint repair, the proposed approach employs a reconstructive joint tunnel drilling locator, or acromioclavicular joint guide, to facilitate compression of a joint and drilling of two holes for repairs and/or rebuilding of the acromioclavicular (AC) and/or coracoclavicular (CC) joint. When the AC/CC joint is ruptured, particular repair techniques require a graft to be passed under the coracoid and form a sling whose ends are anchored in the clavicle. Further, it is desirable to install a suture anchor in the coracoid tied to the clavicle to take the load off the graft during initial healing.

The guide includes two ratcheting sleeves, a central sleeve and a second sleeve pivoting around the axis of the first to allow a second hole to be drilled offset from the first at a known or predetermined distance. The guide includes an aimer arm to provide a target for the first hole and allow compression of the joint, or surgical member being drilled. The sleeves each define an insertion member such as a drill guide for advancement to the entry location of the respective drilling sites. The aimer arm is disposable at an opposed side of a joint from the drilling sites, and is securable for positioning the insertion members for a guidewire or other drilling member. The first member is fixable at a primary location for drilling, and the second member is positionable by rotating the second insertion member about the axis defined by the first insertion member to locate a second drilling site at the predetermined distance and optimal location from the primary location, for drilling a substantially parallel (non-intersecting) tunnel, thus obviating the need for separate right and left or other permutations of a drilling guide.

Configurations herein are based, in part, on the observation that repairs and/or rebuilding of the acromioclavicular (AC)/coracoclavicular (CC) joint may require a graft to be passed under the coracoid and form a sling whose ends are anchored in the clavicle. Further, it is desirable to install a suture anchor in the coracoid tied to the clavicle to take the load off the graft during initial healing. Unfortunately, conventional approaches suffer from the shortcoming that the available guides provide for placement of only a single hole and further require a right and left guide depending on the operative side.

Configurations herein substantially overcome the above described shortcomings by providing a reconstructive joint tunnel locator in the form of an acromioclavicular joint guide for drilling two holes (tunnels) spaced apart by a predetermined distance, and by orienting the drill guides in a pivoting arrangement allowing one drill guide to pivot around the axis of the other at the predetermined distance for locating the second drill hole at the predetermined distance on either the right or left side of a surgical patient.

In an example configuration discussed further below, the acromioclavicular joint guide includes a tunnel locating device for compressing a surgical member between an insertion member and an aimer point to permit an operator, such as a surgeon, to dispose an insertion wire along an axis defined by the insertion member. The device includes a plurality of insertion members including a primary insertion member and moveable, or pivoting, insertion members, such that the pivoting insertion members are disposed at a predetermined distance around a primary insertion axis defined by the primary insertion member.

In the example arrangement, two tunnels are employed corresponding to a primary insertion member and a pivoting, or secondary insertion member. A pivot block has a plurality of apertures forming sleeves in the pivot block for accommodating each of the insertion members, such that each of the sleeves defines an insertion axis for a respective insertion member of the plurality of insertion members. The insertion members are each disposed in a respective sleeve of the pivot block for insertion toward the surgical member along nonintersecting axes defined by the sleeve, such that the insertion members follow generally parallel paths into the surgical member (i.e. bone). An elongated arm attaches to the pivot block at a proximate portion or end and has a aimer point at a distal portion or end, in which the elongated arm may extend around the surgical member via an inverted portion or bend such that the aimer point is on the insertion axis of the primary insertion member. In this manner, the aimer point locates an exit of the hole from the insertion point defined by the primary insertion member, and the pivoting insertion member defines a second tunnel located at the predetermined distance from the primary tunnel.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Disclosed below is an example configuration and deployment of the AC/CC tunnel drilling locator. The tunnel drilling locator operates as a guide for facilitating tunnel placement by an operator of the guide, typically a surgeon. A surgical member such as a patient bone structure is employed as an example in a reconstructive procedure of an AC/CC joint. Other surgical members involving other joints may also benefit from application of the disclosed guide. The example below depicts a particular configuration and usage of the guide; other arrangements and usages, such as those involving additional tunnels, may be apparent to those of skill in the art.

Figure 1:
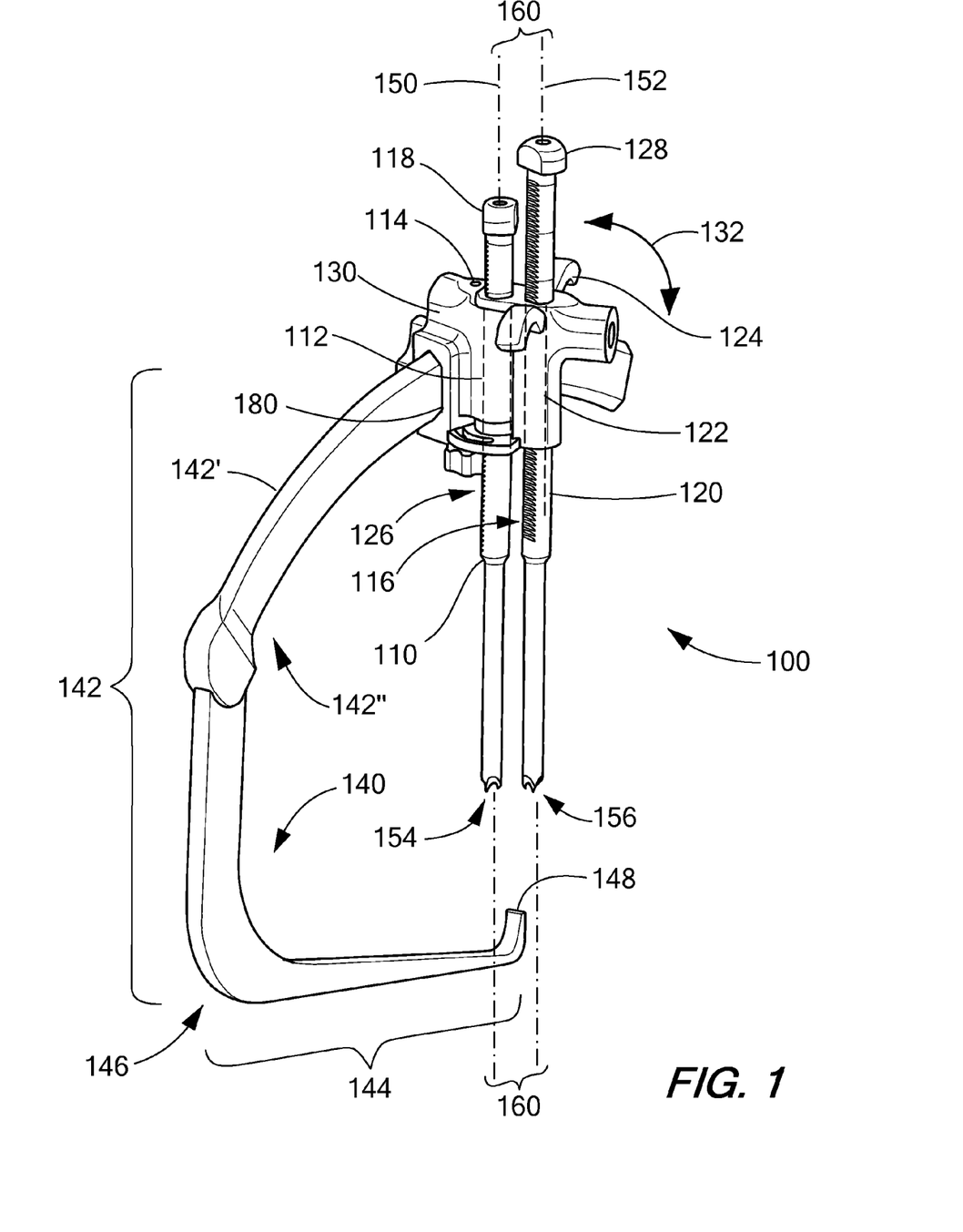
FIG. 1 shows a perspective view of the tunnel drilling locator.

FIG. 1 shows a perspective view of the tunnel drilling locator 100. Referring to FIG. 1, the tunnel drilling locator 100 includes a primary insertion member 110 and a secondary insertion member 120 disposed in sleeves 112, 122 (respectively) through apertures 114, 124 in a pivot block 130. The apertures 114, 124 form sleeves 112, 122 for insertion of the insertion members 110, 120 and adapted for ratcheting movement through the sleeves 112, 122 via ratcheting teeth 116, 126 on the insertion members 110, 120. Each of the insertion members 110, 120 is adapted for ratcheting movement along a primary insertion axis 150 and a secondary insertion axis 152, respectively. An engaging tip 154, 156, on each insertion member 110, 120 (also referred to as a "bullet") fixes the insertion member 110, 120 to surgical members upon sufficient insertion and compression, discussed further below. A knob 118, 128 on each of the insertion members permits insertion force and rotational force for disengaging the teeth and releasing the ratchet.

An elongated arm 140 attaches the pivot block 130 for permitting rotational communication around the primary insertion axis 150, allowing the secondary (moveable, or pivoting) insertion member 120 to rotate or pivot around the primary insertion axis 110 at a predetermined distance 160 determined by the sleeves 112, 122 in the pivot block 130, as shown by arrows 132. The pivot block 130 therefore allows the moveable insertion member to pivot around the primary insertion member 110 to accommodate right or left shoulder positioning while maintaining the fixed distance 160 between the insertion members 110, 120 for optimal drilling placement of tunnels. In a particular configuration, also shown in greater detail in FIG. 4, the pivot block 130 may be adapted to slide off the proximate end 142' of the arm for reverse installation on the opposed side 142" of the proximate end 142 at the tip 147 for pivoting from the opposed side 142".

The elongated arm 140 includes a proximate end 142 and a distal end 144 coupled by a bend 146. The bend 146 allows the proximate end 142 to extend around the surgical member and inverts the arm 140 such that the distal end 144 terminates in an insertion point 148, referring to the flat area proximal and perpendicular to the tip. aligned with the insertion axis 150 such that the primary insertion member 110, when disposed through the sleeve 112 via the ratcheting teeth 126, compresses the surgical members between the aimer point 148 and the engaging tip 154 of the primary insertion member 110 for defining a point of insertion for an insertion wire or other drilling tool. Subsequent to fixing the primary insertion point, the pivoting insertion member 120 may pivot for defining a secondary insertion point allowing optimal hole position in a surgical member, (e.g. a clavicle of a surgical patient) defined by advancement of the moveable insertion member 120 at the predetermined distance 160 on the surgical member to dispose the engaging tip 156 of the pivoting insertion member 120.

Figure 2:
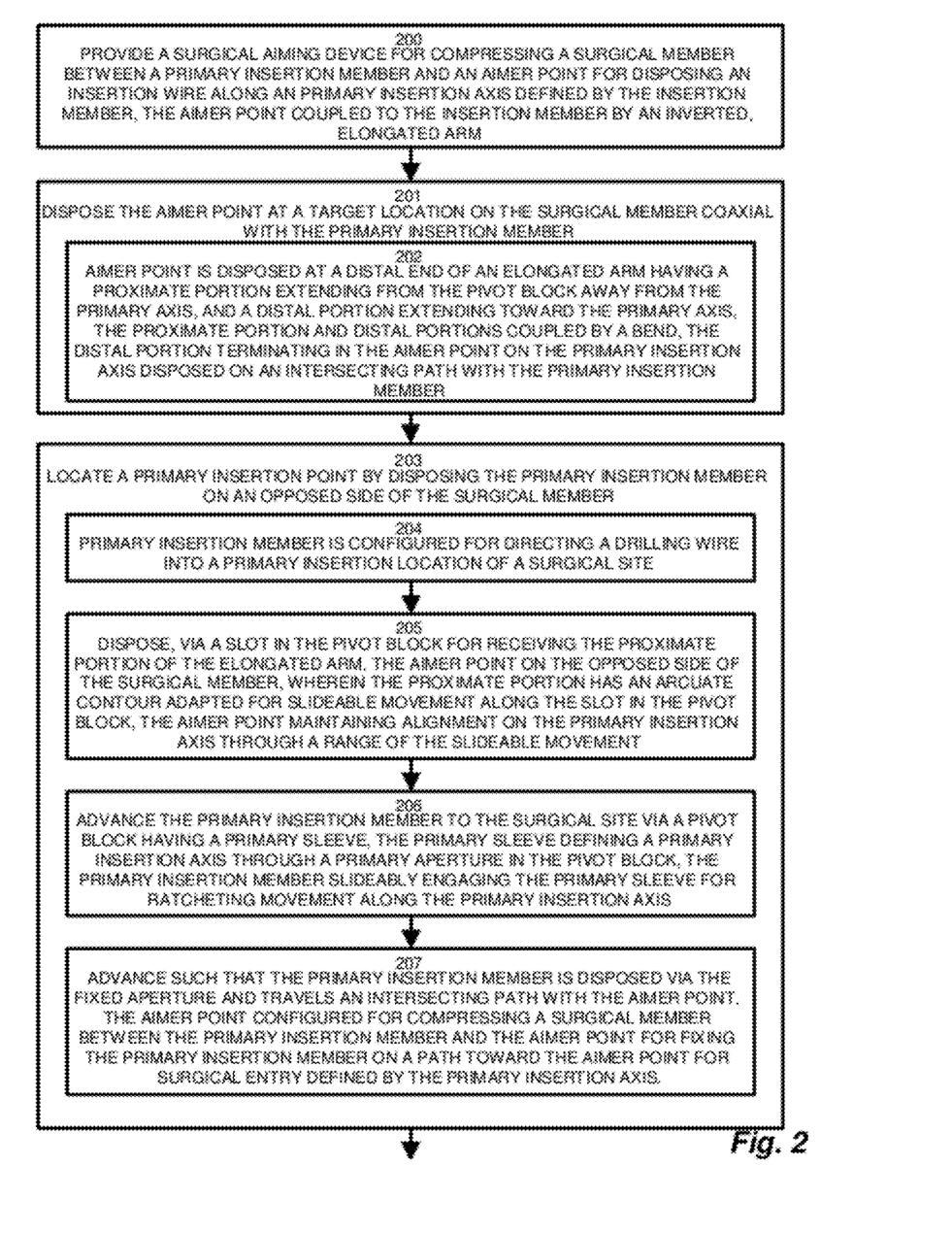
FIGS. 2-3 show a flowchart of tunnel locating using the tunnel drilling locator of FIG. 1 for use with an insertion wire.
Figure 3:
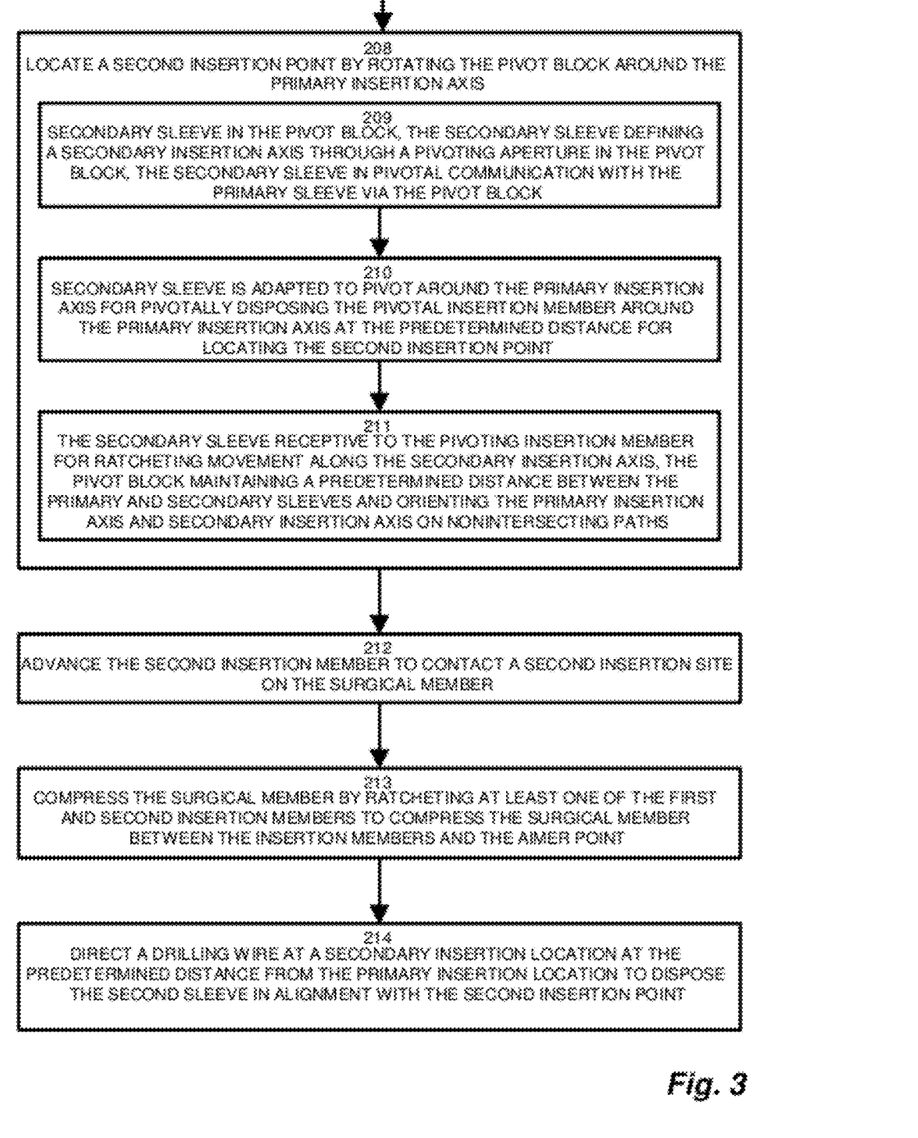

FIGS. 2-3 show a flowchart of tunnel locating using the tunnel drilling locator 100. One particular use of the drill guide device is for an acromioclavicular joint repair for drilling two holes (tunnels) spaced apart by a predetermined distance. The method for locating insertion sites for surgical joint repair of a surgical joint member such as the acromioclavicular/coracoclavicular joint as performed by an operator (surgeon) includes, at step 200, providing a surgical aiming device 100 for compressing a surgical member between a primary insertion member 110 and an aimer point 148. The insertion member 110 is typically a drill guide or other elongated structure having a bore for delivering an insertion wire. The aimer point 148 locates an exit point for disposing an insertion wire 170 (FIG. 4) along the primary insertion axis 150 defined by the insertion member 110, such that the aimer point 148 is coupled to the primary insertion member 110 by an inverted, elongated arm 140 coupling the aimer point 148 to the insertion members 110, 120 around opposed sides of a surgical member.

The operator disposes the aimer point 148 at a target location on the surgical member coaxial with the primary insertion member 110, as depicted at step 201. The aimer point 148 is disposed at a distal end of an elongated arm 140 having a proximate end 142 extending from the pivot block 130 away from the primary axis 150, and a distal end 144 extending toward the primary axis 150, the proximate end 142 and distal end 144 coupled by a bend 146, in which the distal end 144 terminates in the aimer point 148 which is located on the primary insertion axis 150 disposed on an intersecting path with the primary insertion member 110, as disclosed at step 202.

The operator locates a primary insertion point by disposing the primary insertion member 110 and engaging tip 154 on an opposed side of the surgical member, as depicted at step 203. Once the aimer point 148 is located (set) at the drilling terminus and affixed by the pointed end, the primary insertion member 110 allows the operator to locate the start of the tunnel for drilling. The primary insertion member is configured for directing the drilling wire 170 into a primary insertion location of a surgical site, as shown at step 204. Locating the primary insertion member 110 may also include disposing, via a slot 180 in the pivot block 130 for receiving the proximate end 142 of the elongated arm 140, the aimer point 148 on the opposed side of the surgical member, as depicted at step 205, to change the angle of the distal end 144. The proximate end 142 has an arcuate contour adapted for slideable movement along the slot 180 in the pivot block 130, while the aimer point 148 maintains alignment on the primary insertion axis 150 through a range of the slideable movement. Such slideable movement allows optimal placement of the insertion member 150 and the aimer point 148 on opposed sides of the surgical member.

The operator begins advancing the primary insertion member 110 to the surgical site via the pivot block 130 having a primary sleeve 112, such that the primary sleeve 112 defines the primary insertion axis 150 through a primary aperture 114 in the pivot block 130, as disclosed at step 206. The primary insertion member 150 slideably engages the primary sleeve 112 for ratcheting movement along the primary insertion axis 150 via ratcheting teeth 126 on the primary insertion member 110. Advancing the primary insertion member 110 includes advancing such that the primary insertion member 110 is disposed via the fixed (non-pivoting) aperture 114 and travels an intersecting path with the aimer point 148, in which the aimer point 148 is configured for compressing a surgical member between the primary insertion member 110 and the aimer point 148 for fixing the primary insertion member 110 on a path toward the aimer point 148 for surgical entry defined by the primary insertion axis 150, as depicted at step 207.

Once the location of the primary tunnel is identified, the pivot block 130 is employed to identify second tunnel at a predetermined distance around the primary tunnel. The operator locates a second insertion point by rotating the pivot block 130 around the primary insertion axis 100, as depicted at step 208. To locate the tunnel, the pivot block 130 includes a secondary sleeve 122 in the pivot block 130, such that the secondary sleeve 122 defines a secondary insertion axis 152 through a pivoting aperture 124 in the pivot block 130, in which the secondary sleeve 122 is in pivotal communication with the primary sleeve 112 via the pivot block 130, as shown at step 209. The secondary sleeve 122 is adapted to pivot around the primary insertion axis 150 for pivotally disposing the pivoting insertion member 120 around the primary insertion axis 150 at the predetermined distance 160 for locating the second insertion point with engaging tip 156, as depicted at step 210. The operator disposes the pivoting insertion member 120, in which the secondary sleeve 122 is receptive to the pivoting insertion member 120 for ratcheting movement along the secondary insertion axis 152, as disclosed at step 211. The pivot block 130 maintains a predetermined distance 160 between the primary 112 and secondary sleeves 122 and orients the primary insertion axis 150 and secondary insertion axis 152 on nonintersecting paths for forming parallel tunnels, as depicted at step 211.

The operator advances the second insertion member 120 to contact a second insertion site on the surgical member with the engaging tip 156, as disclosed at step 212, and compresses the surgical member by ratcheting at least one of the first and second insertion members 110, 120 to compress the surgical member between the insertion members and the aimer point 148, as depicted at step 213. As the primary insertion member is typically located first, the primary insertion member 110 and the aimer point 148 compress the surgical member uniformly due to axial alignment on the primary insertion axis 150. The secondary insertion member 120 is then positioned by rotating, or pivoting of the pivot block 130. Once both insertion members 110, 120 are fixed, the operator directs a drilling wire 170 via the primary insertion member 110, and at the secondary insertion location at the predetermined distance 160 from the primary insertion location to dispose the second sleeve in alignment with the second insertion point, as depicted at step 214.

Figure 4:
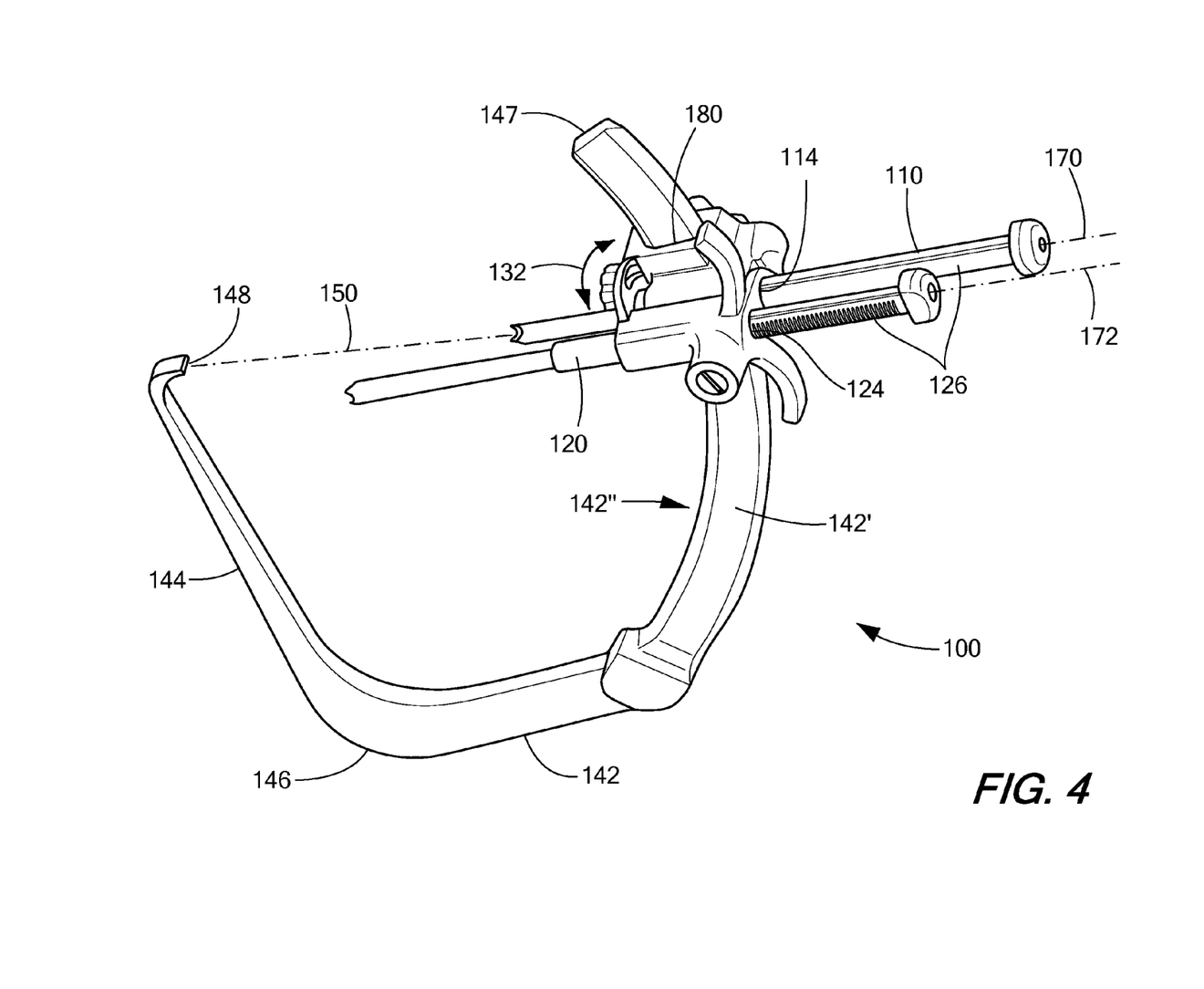
FIG. 4 shows a perspective downward view of the tunnel drilling locator of FIG. 1.

FIG. 4 shows a perspective downward view of the tunnel drilling locator of FIG. 1. Referring to FIGS. 1 and 4, an insertion wire 170, 172 is insertable through the insertion members 110, 120, respectively, for drilling the primary and secondary tunnels. Pivotal movement 132 of the pivoting insertion member 120 is along a side 142' of the proximate end 142 of the elongated arm 140, or the pivot block 130 may be disposed along the arm to a tip 147 for pivoting along the opposed side 142" or for removal and reinstallation of the pivot block 130.

Figure 5:
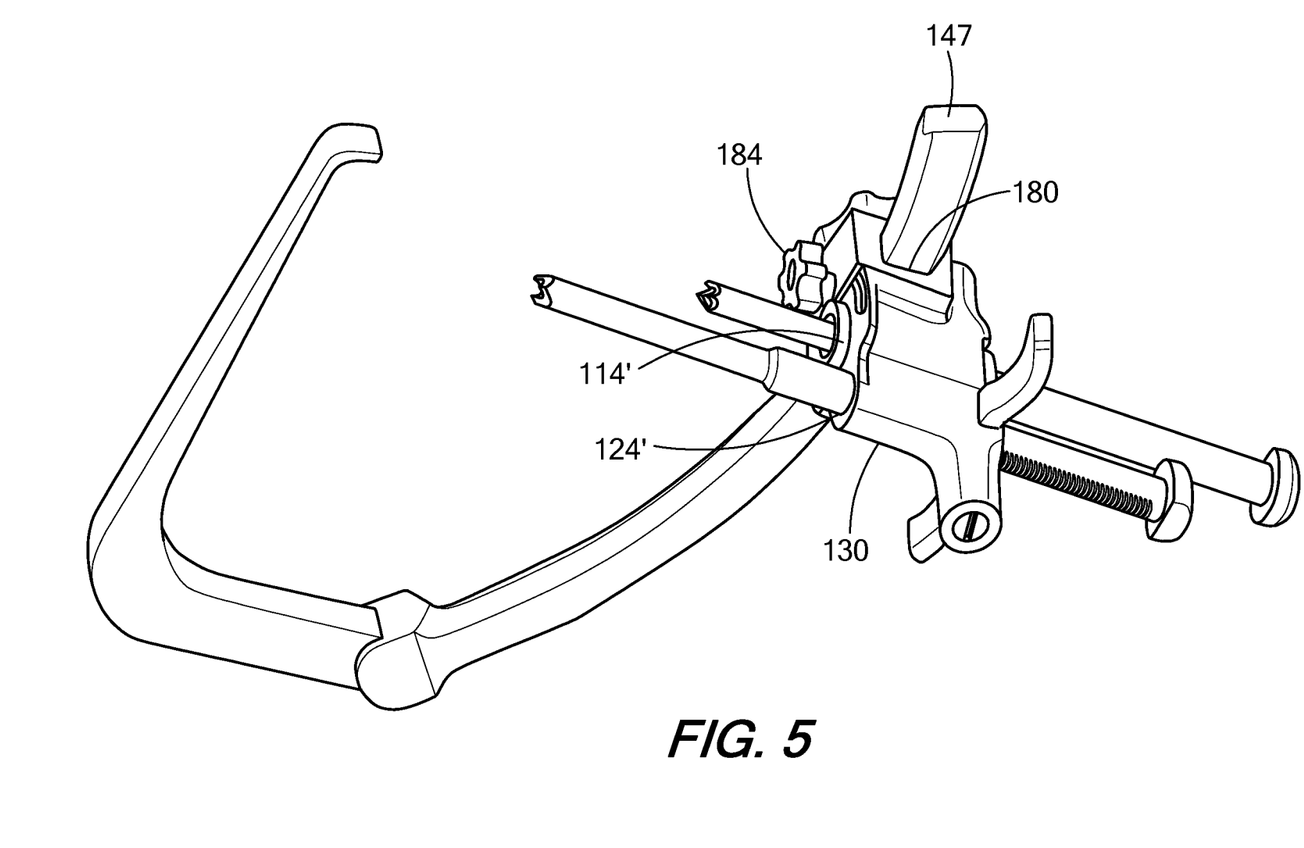
FIG. 5 shows a perspective upward view of the tunnel drilling locator of FIG. 1.

FIG. 5 shows a perspective upward view of the tunnel drilling locator of FIG. 1. Referring to FIGS. 1 and 5, a knob 130 secures the pivot block 130 to the proximate end 142 via a threaded screw or other suitable mechanism. Exit apertures 114' and 124' define the exit points of the sleeves 112, 122 corresponding to apertures 114 and 124, respectively.

Figure 6:
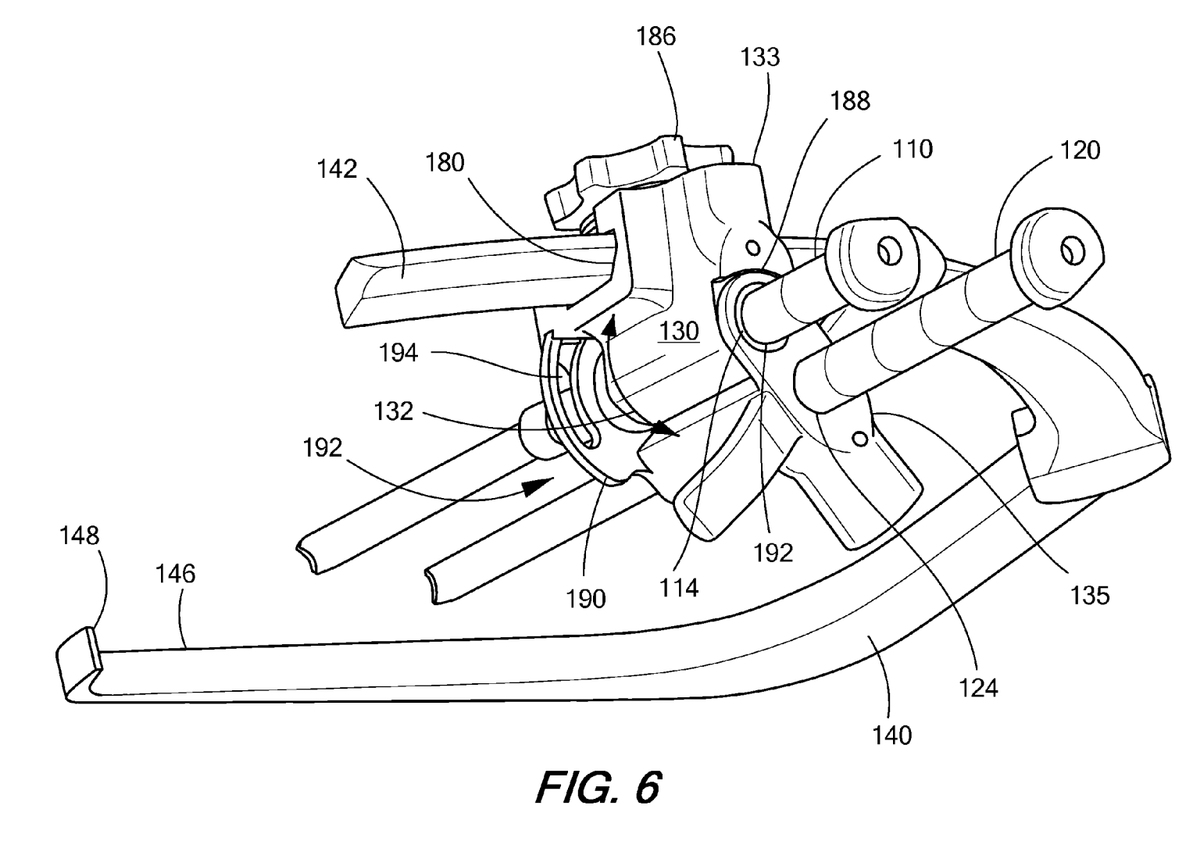
FIG. 6 shows a top perspective angle view of the tunnel drilling locator.

FIG. 6 shows a top perspective angle view of the tunnel drilling locator. Referring to FIGS. 1, 4 and 6, the pivot block 130 includes a slideable portion 133 and a rotating portion 135. The slideable portion 133 includes the slot 180 responsive to the proximate end 142 of the elongated arm 140 for arcuate, sliding movement thereto. A fixing knob 186 turns a screw for fixing the pivot block on the arm 140. The rotating portion 135 couples to the slideable portion 133 by a top bracket 188 and a bottom bracket 190 secured in rotational communication by the primary insertion member 110 passing through hinge apertures 192 in the top and bottom brackets 188, 190. A guide slot 194 in the bottom bracket 190 defines the pivoting (rotational) movement range 132. In this manner, the secondary insertion member 120 is permitted pivotal movement around the primary insertion member 110 while both are afforded slideable movement along the proximate end 142 relative to the aimer tip 148.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A tunnel locating device for compressing a surgical member between an insertion member and an aimer point for disposing an insertion wire along an axis defined by the insertion member, comprising: a plurality of insertion members including a primary insertion member and at least one moveable insertion member including a secondary insertion member, the at least one moveable insertion member disposed at a predetermined distance around a primary insertion axis defined by the primary insertion member; a pivot block having a plurality of apertures forming sleeves in the pivot block, each of the sleeves defining an insertion axis for a respective insertion member of the plurality of insertion members; an elongated arm attached to the pivot block at a proximate end and having the aimer point at a distal end, the aimer point on the insertion axis of the primary insertion member; the insertion members each disposed in a respective sleeve of the pivot block for insertion toward the surgical member along nonintersecting axes defined by the sleeve, the nonintersecting axes of the insertion members being generally parallel and at a fixed distance with respect to each other; and the pivot block maintaining at least one of the apertures fixed along the axis aligned with the aimer point, such that the primary insertion member is disposed via the fixed aperture and travels an intersecting path with the aimer point, the aimer point configured for compressing a surgical member between the primary insertion member and the aimer point for fixing the primary insertion member on a path toward the aimer point for surgical entry defined by the primary insertion axis.

2. The device of claim 1 further comprising an inversion in the elongated arm, the inversion having an angular bend defining the proximate end and the distal end for disposing the aimer point on an opposed side of the surgical member from the primary insertion member.

3. The device of claim 2 wherein the proximate end of the elongated arm extends from the pivot block away from the primary insertion axis, and the distal end extends toward the primary insertion axis, the proximate end and the distal end coupled by the angular bend, the distal end terminating on the primary insertion axis in the aimer point and disposed on an intersecting path with the primary insertion member.

4. The device of claim 1 wherein the primary insertion member is adapted for ratcheting movement on an intersecting path with the aimer point, the ratcheting movement compressing the surgical member between the aimer point and the primary insertion member for fixing an insertion location for an insertion wire.

5. The device of claim 4 further comprising:
a slot in the pivot block for receiving the proximate end of the elongated arm, wherein the proximate end has an arcuate contour adapted for slideable movement along the slot in the pivot block, the aimer point maintaining alignment on the primary insertion axis through a range of the slideable movement.

6. The device of claim 1 wherein the sleeves include a primary sleeve and a pivotal sleeve, the primary sleeve defining the primary insertion axis and the pivotal sleeve disposed in a pivoting manner about the primary insertion axis by rotating around the primary sleeve.

7. The device of claim 6 further comprising a set of ratcheting teeth on each of the insertion members, the ratcheting teeth responsive to a pawl disposed in the sleeves for adapting the insertion members for ratcheting movement toward the surgical member.

8. The device of claim 1 wherein the plurality of sleeves is defined by a primary sleeve receptive to the primary insertion member, and a pivotal sleeve receptive to a pivoting insertion member defined by one of the secondary insertion member disposed in the pivotal sleeve;
the pivot block adapted for rotation about a primary insertion axis defined by the primary sleeve;
the primary insertion member adapted for slideable movement along the primary insertion axis; and
the pivotal sleeve adapted to pivot around the primary insertion axis for pivotally disposing the pivoting insertion member around the primary insertion axis at the predetermined distance.

9. The device of claim 8 wherein the primary insertion member and the pivoting insertion member are adapted for nonconverging movement along respective axes for contacting the surgical site at respective locations separated by the predetermined distance defined by the primary and pivot sleeves in the pivot block.

10. The device of claim 1 wherein the surgical member is a skeletal joint, wherein insertion wires are configured to form holes defined by the insertion members in the skeletal joint, the holes being configured for placement of reconstructive connective tissue.

11. A surgical guide comprising:
a primary insertion member configured for directing a drilling wire into a primary insertion location of a surgical site;
a pivot block having a primary sleeve, the primary sleeve defining a primary insertion axis through a primary aperture in the pivot block, the primary insertion member slideably engaging the primary sleeve for ratcheting movement along the primary insertion axis;
a secondary sleeve in the pivot block, the secondary sleeve defining a secondary insertion axis through a pivoting aperture in the pivot block, the secondary sleeve in pivotal communication with the primary sleeve via the pivot block;
a pivoting insertion member, the secondary sleeve receptive to the pivoting insertion member for ratcheting movement along the secondary insertion axis, the pivot block maintaining a predetermined distance between the primary and secondary sleeves and orienting the primary insertion axis and secondary insertion axis on generally parallel, nonintersecting paths for directing a drilling wire at a secondary insertion location at the predetermined distance from the primary insertion location; and
an elongated arm having a proximate end extending from the pivot block away from the primary axis, and a distal end extending toward the primary axis, the proximate end and distal ends coupled by a bend, the distal end terminating in an aimer point on the primary insertion axis disposed on an intersecting path with the primary insertion member, the pivot block maintaining at least one of the apertures fixed along the axis aligned with the aimer point, such that the primary insertion member is disposed via the fixed aperture and travels an intersecting path with the aimer point, the aimer point configured for compressing a surgical member between the primary insertion member and the aimer point for fixing the primary insertion member on a path toward the aimer point for surgical entry defined by the primary insertion axis,
wherein the primary insertion axis and secondary insertion axis are at a fixed distance with respect to each other.

12. A tunnel locating device for compressing a surgical member between an insertion member and an aimer point for disposing an insertion wire along an axis defined by the insertion member, comprising: a plurality of insertion members including a primary insertion member and at least one moveable insertion member including a secondary insertion member, the at least one moveable insertion member disposed at a predetermined distance around a primary insertion axis defined by the primary insertion member; a pivot block having a plurality of apertures forming sleeves in the pivot block, each of the sleeves defining an insertion axis for a respective insertion member of the plurality of insertion members; the insertion members each disposed in a respective sleeve of the pivot block for insertion toward the surgical member along nonintersecting axes defined by the sleeve; and an elongated arm attached to the pivot block at a proximate end and having an aimer point at a distal end, the aimer point being on the insertion axis of the primary insertion member; wherein the pivot block allows for rotation of the sleeves around the primary insertion axis, and wherein the insertion axes of the sleeves remain generally parallel to each other throughout such rotation.

* * * * *